US008877023B2

(12) United States Patent
Whyte et al.

(10) Patent No.: US 8,877,023 B2
(45) Date of Patent: Nov. 4, 2014

(54) ELECTROCHEMICAL-BASED ANALYTICAL TEST STRIP WITH INTERSECTING SAMPLE-RECEIVING CHAMBERS

(75) Inventors: Lynsey Whyte, Inverness (GB); Scott Sloss, Inverness (GB); Neil Whitehead, Inverness (GB); David McColl, Inverness (GB); Antony Smith, Inverness (GB)

(73) Assignee: Lifescan Scotland Limited, Inverness (GB)

( * ) Notice: Subject to any disclaimer, the term of this patent is extended or adjusted under 35 U.S.C. 154(b) by 168 days.

(21) Appl. No.: 13/529,890

(22) Filed: Jun. 21, 2012

(65) Prior Publication Data
US 2013/0341208 A1  Dec. 26, 2013

(51) Int. Cl.
*G01N 27/327*   (2006.01)
*C12Q 1/54*     (2006.01)
*G01N 33/66*    (2006.01)
*C12Q 1/00*     (2006.01)

(52) U.S. Cl.
CPC ............ *G01N 27/327* (2013.01); *C12Q 1/004* (2013.01)
USPC ................... 204/403.1; 435/287.1; 422/68.1; 422/82.01

(58) Field of Classification Search
CPC ............ C12Q 1/006; C12Q 1/54; C12Q 1/00; G01N 33/64; G01N 33/66; G01N 2333/904; G01N 27/3272; G01N 27/327
USPC ............ 204/403.01–403.15; 422/68.1, 82.01; 435/287.1
See application file for complete search history.

(56) References Cited

U.S. PATENT DOCUMENTS

| | | | |
|---|---|---|---|
| 4,945,313 | A | 7/1990 | Brilka et al. |
| 5,708,247 | A | 1/1998 | McAleer et al. |
| 5,951,836 | A | 9/1999 | McAleer et al. |
| 6,241,862 | B1 | 6/2001 | McAleer et al. |
| 6,284,125 | B1 | 9/2001 | Hodges et al. |
| 6,377,894 | B1 | 4/2002 | Deweese et al. |
| 6,488,827 | B1 | 12/2002 | Shartle |
| 6,521,182 | B1 | 2/2003 | Shartle |

(Continued)

FOREIGN PATENT DOCUMENTS

| | | |
|---|---|---|
| EP | 1304570 A1 | 4/2003 |
| WO | WO 2005/001462 A1 | 1/2005 |
| WO | WO 2010/049669 A1 | 5/2010 |

OTHER PUBLICATIONS

L. Shrimanth Sudheer, et al. "Microcontroller based phase meter," Journal of Instrument Soc. of India, KA, India, Mar. 2009, vol. 39 No. 1, pp. 62-64.

(Continued)

*Primary Examiner* — Jennifer Dieterle

(57) ABSTRACT

An electrochemical-based analytical test strip for the determination of an analyte (such as glucose) in a bodily fluid sample (for example, a whole blood sample) and/or a characteristic of the bodily fluid sample (for example, hematocrit) includes a first sample-receiving chamber with first and second sample-application openings, and first and second electrodes. The first and second electrodes are disposed in the first sample-receiving chamber between the first and second sample-application openings. The electrochemical-based analytical test strip also includes a second sample-receiving chamber and a plurality of electrodes disposed in the second sample-receiving chamber. In addition, the second sample-receiving chamber intersects the first sample-receiving chamber between the first and second electrodes, thereby defining a chamber intersection.

2 Claims, 4 Drawing Sheets

(56) References Cited

U.S. PATENT DOCUMENTS

| | | |
|---|---|---|
| 6,676,815 B1 | 1/2004 | Bhullar et al. |
| 6,733,655 B1 | 5/2004 | Davies et al. |
| 7,022,286 B2 | 4/2006 | Lemke et al. |
| 7,144,485 B2 * | 12/2006 | Hsu et al. ............... 204/403.02 |
| 7,199,594 B2 | 4/2007 | Kermani |
| 7,323,098 B2 | 1/2008 | Miyashita et al. |
| 7,338,639 B2 | 3/2008 | Burke et al. |
| 7,718,439 B2 | 5/2010 | Groll |
| 7,955,484 B2 | 6/2011 | Cai et al. |
| 8,012,428 B2 | 9/2011 | Dilleen et al. |
| 2005/0023136 A1 | 2/2005 | Leach et al. |
| 2005/0023137 A1 | 2/2005 | Bhullar et al. |
| 2005/0023152 A1 | 2/2005 | Surridge et al. |
| 2005/0114062 A1 * | 5/2005 | Davies et al. ............... 702/104 |
| 2007/0084734 A1 | 4/2007 | Roberts et al. |
| 2007/0087397 A1 | 4/2007 | Kraft et al. |
| 2007/0123801 A1 | 5/2007 | Goldberger et al. |
| 2007/0131565 A1 * | 6/2007 | Fujiwara et al. ........... 205/777.5 |
| 2007/0199818 A1 * | 8/2007 | Petyt et al. ............... 204/403.01 |
| 2008/0083618 A1 * | 4/2008 | Neel et al. ................ 204/403.14 |
| 2009/0095623 A1 | 4/2009 | Boiteau et al. |
| 2010/0170791 A1 | 7/2010 | Lee |
| 2010/0270174 A1 | 10/2010 | Chen et al. |
| 2010/0326846 A1 | 12/2010 | Leong |
| 2011/0094896 A1 | 4/2011 | Macfie et al. |
| 2011/0155585 A1 * | 6/2011 | Chatelier et al. ........... 205/777.5 |
| 2011/0155589 A1 * | 6/2011 | Chatelier et al. .............. 205/782 |

OTHER PUBLICATIONS

International Search Report, PCT Application No. PCT/EP2013/062950, European Patent Office, Rijswijk, NL, Aug. 16, 2013, 4 pages.

* cited by examiner

ELECTROCHEMICAL-BASED ANALYTICAL TEST STRIP WITH INTERSECTING SAMPLE-RECEIVING CHAMBERS

BACKGROUND OF THE INVENTION

1. Field of the Invention

The present invention relates, in general, to medical devices and, in particular, to analytical test strips and related methods.

2. Description of Related Art

The determination (e.g., detection and/or concentration measurement) of an analyte in a fluid sample is of particular interest in the medical field. For example, it can be desirable to determine glucose, ketone bodies, cholesterol, lipoproteins, triglycerides, acetaminophen and/or HbA1c concentrations in a sample of a bodily fluid such as urine, blood, plasma or interstitial fluid. Such determinations can be achieved using analytical test strips, based on, for example, visual, photometric or electrochemical techniques. Conventional electrochemical-based analytical test strips are described in, for example, U.S. Pat. Nos. 5,708,247, and 6,284,125, each of which is hereby incorporated in full by reference.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention, in which.

DETAILED DESCRIPTION OF ILLUSTRATIVE EMBODIMENTS

Figure 1:
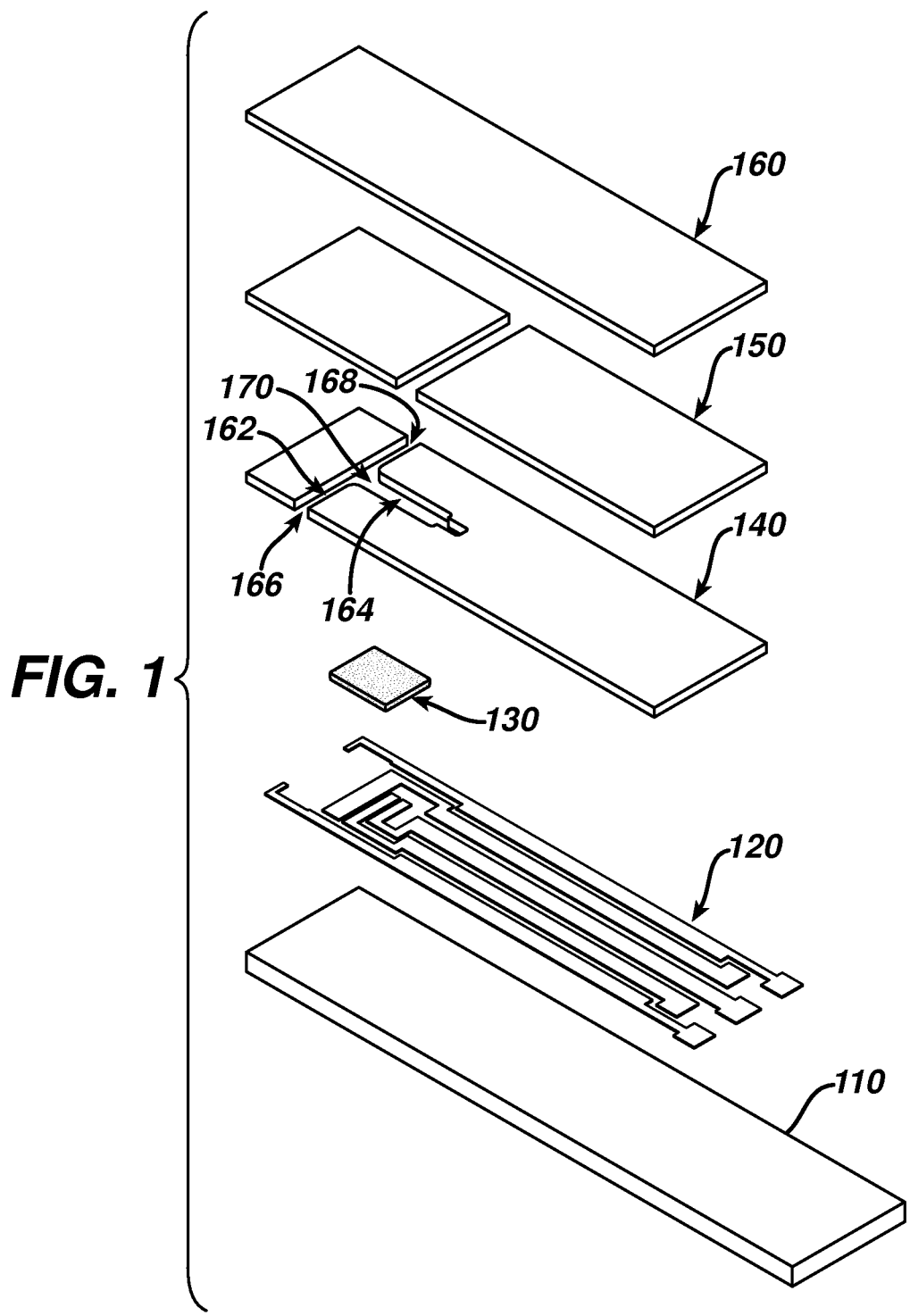
FIG. 1 is a simplified exploded view of an electrochemical-based analytical test strip according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

As used herein, the terms "intersect" and "intersecting" refers to entities (such as a first sample-receiving chamber and a second sample-receiving chamber) forming an intersection with each other; crossing each other, or overlapping each other. In addition, as used herein, the term "intersection" refers to a point or set of points common to two or more geometric entities (such as two sample-receiving chambers).

In general, an electrochemical-based analytical test strip for the determination of an analyte (such as glucose) in a bodily fluid sample (for example, a whole blood sample) and/or a characteristic of the bodily fluid sample (for example, hematocrit) includes a first sample-receiving chamber with first and second sample-application openings, and first and second electrodes. The first and second electrodes are disposed in the first sample-receiving chamber between the first and second sample-application openings. The electrochemical-based analytical test strip also includes a second sample-receiving chamber and a plurality of electrodes disposed in the second sample-receiving chamber. In addition, the second sample-receiving chamber intersects the first sample-receiving chamber between the first and second electrodes, thereby defining a chamber intersection.

Electrochemical-based analytical test strips according to embodiments of the present invention are beneficial in that, for example, a relatively small volume of bodily fluid sample (for example, a bodily fluid sample of approximately 1.3 micro-liters) can be employed to fill both the first and second sample-receiving chambers. Such a relatively small bodily fluid sample is enabled since the chamber intersection serves as the bodily fluid sample entrance to the second sample-receiving chamber and either of the first and second sample-application openings can be employed to apply a bodily fluid sample that fills both the first and the second sample-receiving chambers. In addition, since the first and second electrodes disposed in the first sample-receiving chamber are on either side of the chamber intersection, a beneficially large separation of the first and second electrodes is achieved while maintaining a low bodily fluid sample volume. Moreover, electrochemical-based analytical test strips according to embodiments of the present invention can be manufactured using relatively inexpensive and simple conventional processes and materials.

Figure 2:
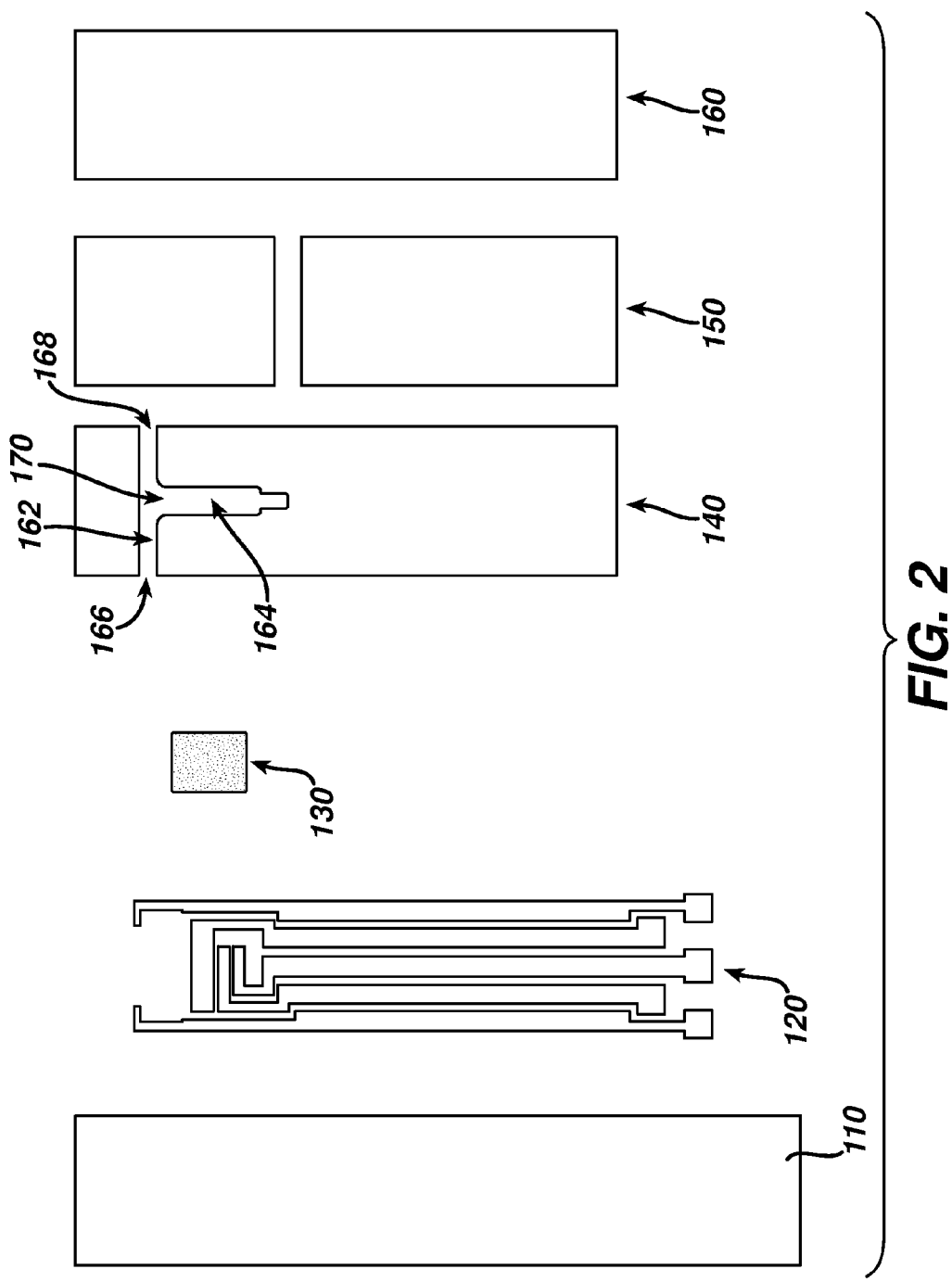
FIG. 2 is a sequence of simplified top views of the various layers of the electrochemical-based analytical test strip of FIG. 1.
Figure 3:
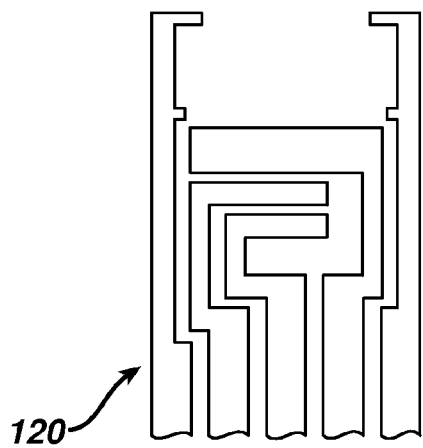
FIG. 3 is a simplified top view representation of a portion of a patterned conductor layer of the electrochemical-based analytical test strip of FIG. 1.
Figure 4:
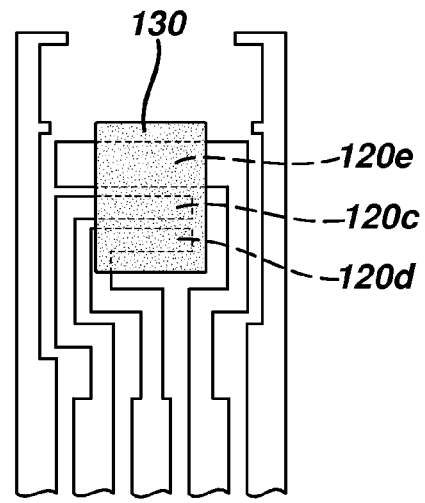
FIG. 4 is a simplified top view of the portion of the patterned conductor layer and an enzymatic reagent layer of the electrochemical-based analytical test strip of FIG. 1 with the reagent layer depicted as partially transparent to highlight the patterned conductor layer there under.
Figure 5:
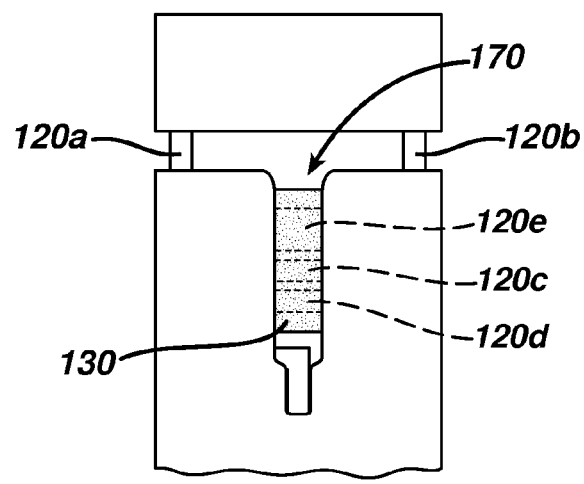
FIG. 5 is a simplified top view of the portion of the patterned conductor layer, the enzymatic reagent layer and a portion of a patterned spacer layer of the electrochemical-based analytical test strip of FIG. 1.

FIG. 1 is a simplified exploded view of an electrochemical-based analytical test strip 100 according to an embodiment of the present invention. FIG. 2 is a sequence of simplified top views of various layers of electrochemical-based analytical test strip 100. FIG. 3 is a simplified top view of a portion of a patterned conductor layer of electrochemical-based analytical test strip 100. FIG. 4 is a simplified top view of a portion of the patterned conductor layer and an enzymatic reagent layer of electrochemical-based analytical test strip 100, with the enzymatic reagent layer depicted as partially transparent to highlight the patterned conductor layer thereunder. FIG. 5 is a simplified top view of the portion of the patterned conductor layer, the enzymatic reagent layer and a portion of a patterned spacer layer of electrochemical-based analytical test strip 100.

Referring to FIGS. 1-5, electrochemical-based analytical test strip 100 for the determination of an analyte (such as glucose) in a bodily fluid sample (for example, a whole blood sample) includes an electrically-insulating substrate layer 110, a patterned conductor layer 120, an enzymatic reagent layer 130, a patterned spacer layer 140, a hydrophilic layer 150, and a top layer 160.

The disposition and alignment of electrically-insulating substrate layer 110, patterned conductor layer 120 (which includes a first electrode 120a, second electrode 120b, working electrode 120c, working electrode 120d and counter/reference electrode 120e; see FIGS. 4 and 5 in particular), patterned spacer layer 140, hydrophilic layer 150 and top layer 160 of electrochemical-based analytical test strip 100 are such that a first sample-receiving chamber 162 and a second sample-receiving chamber 164 are defined within electrochemical-based analytical test strip 100. Moreover, first sample-receiving chamber 162 includes a first sample-application opening 166 and a second sample-application opening 168.

In the embodiment of FIGS. 1-5, first electrode 120a is disposed in the first sample-receiving chamber 162 between the first sample-application opening 166 and the second sample-application opening 168 and second electrode 120b disposed in first sample-receiving chamber 162 between the first sample-application opening 166 and the second sample-application opening 168. Moreover, second sample-receiving chamber 164 intersects the first sample-receiving chamber 162 between the first electrode 120a and the second electrode 120b, thereby defining a chamber intersection 170 in electrochemical-based analytical test strip 100. In addition, electrodes 120c, 120d, and 120e are operatively disposed in second sample-receiving chamber 164.

Although, for the purpose of explanation only, electrochemical-based analytical test strip 100 is depicted as including a total of five electrodes, embodiments of electrochemical-based analytical test strips, including embodiments of the present invention, can include any suitable number of electrodes. First and second electrodes 120a and 120b, respectively, can have areas of, for example, 0.23 square-mm. Working electrodes 120c and 120d can each have, for example, an area of 0.28 square-mm and counter/reference electrode 120e can have, for example, an area of 0.56 square-mm. The distance between the midpoints of the first and second electrodes (i.e., in the left-to-right direction of FIG. 5) is, for example, 4.60 mm.

Patterned conductor layer 120, including electrodes 120a, 120b, 120c, 120d and 120e, of analytical test strip 100 can be formed of any suitable material including, for example, gold, palladium, platinum, indium, titanium-palladium alloys and electrically conducting carbon-based materials including carbon inks. Referring in particular to FIG. 5, the disposition of first working electrode 120c, second working electrode 120d and counter/reference electrode 120e and enzymatic reagent layer 130 are such that analytical test strip 100 is configured for the electrochemical determination of an analyte (glucose) in a bodily fluid sample (whole blood) that has filled second sample-receiving chamber 164.

Moreover, first electrode 120a and second electrode 120b are disposed in first sample-receiving chamber 162 such that electrochemical-based analytical test strip 100 is configured for the determination of haematocrit in a whole blood sample that has filled first sample-receiving chamber 162. During use, a bodily fluid sample is applied to electrochemical-based analytical test strip 100 and transferred to both first sample-receiving chamber 162 (thereby operatively contacting the first and second electrodes 120a and 120b) and to the second sample-receiving chamber 164, thereby operatively contacting electrodes 120c, 120d and 120e. The determination of haematocrit using electrodes of an analytical test strip is described in, for example, U.S. patent application Ser.Nos. 61/581,100; 61/581,097; 61/581,089; 61/530,795 and 61/530,808, each of which is hereby incorporated in full by reference.

Chamber intersection 170 is configured to serve both as a portion of first sample-receiving chamber 162 and as a sample entrance for second sample-receiving chamber 164. Such a configuration beneficially minimizes the volume of the first and second sample-receiving chamber. Moreover, since first sample-receiving chamber 162 is reagent-less (i.e., enzymatic reagent layer 130 is not disposed within first sample-receiving chamber 162), there is no risk of a bodily fluid sample that flows through first sample-receiving chamber inadvertently introducing an unwanted reagent into the second sample-receiving chamber.

In the embodiment of FIGS. 1 through 5, the first sample-receiving chamber 162 and second sample-receiving chamber 164 are disposed in an essentially T-shaped configuration. Such a T-shaped configuration enables first and second sample-application openings 166 and 168 to be disposed on opposing lateral edges of electrochemical-based analytical test strip 100. A user is thus enabled to choose either of the sample-application openings for application of a bodily fluid sample. In the perspective of FIG. 5, first sample-receiving chamber 162 has a width (in the vertical direction of the perspective of FIG. 5) of, for example, 0.75 microns while second sample-receiving chamber 164 has a width (in the horizontal direction of the perspective of FIG. 5) in the vicinity of the electrodes of, for example, 1.3 microns.

A benefit of the T-shaped configuration depicted in, for example, FIGS. 1, 2 and 5) is that the T-shape is symmetrical about a vertical center-line (in the perspective of FIG. 5) of the electrochemical-based analytical test strip. Therefore, it is postulated without being bound that the performance of electrochemical-based analytical test strip 100 would be beneficially identical regardless of whether the first sample-application opening 166 or the second sample-application opening 168 is employed during sample application.

Electrically-insulating substrate layer 110 can be any suitable electrically-insulating substrate layer known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, or a polyester substrate. The electrically-insulating substrate layer can have any suitable dimensions including, for example, a width dimension of about 5 mm, a length dimension of about 27 mm and a thickness dimension of about 0.5 mm.

Electrically-insulating substrate layer 110 provides structure to electrochemical-based analytical test strip 100 for ease of handling and also serves as a base for the application (e.g., printing or deposition) of subsequent layers (e.g., a patterned conductor layer). It should be noted that patterned conductor layers employed in analytical test strips according to embodiments of the present invention can take any suitable shape and be formed of any suitable materials including, for example, metal materials and conductive carbon materials.

Patterned spacer layer 140 can be formed, for example, from a screen-printable pressure sensitive adhesive commercially available from Apollo Adhesives, Tamworth, Staffordshire, UK. In the embodiment of FIGS. 1 through 5, patterned spacer layer 140 defines outer walls of the first sample-receiving chamber 162 and the second sample-receiving chamber 164. Patterned spacer layer 140 can have a thickness of, for example, approximately 130 microns.

Hydrophilic layer 150 can be, for example, a clear film with hydrophilic properties that promote wetting and filling of electrochemical-based analytical test strip 100 by a fluid sample (e.g., a whole blood sample). Such clear films are commercially available from, for example, 3M of Minneapolis, Minn. U.S.A. and Coveme (San Lazzaro di Savena, Italy). Hydrophilic layer 150 can be, for example, a polyester film coated with a surfactant that provides a hydrophilic contact angle<10 degrees. Hydrophilic layer 150 can also be a polypropylene film coated with a surfactant or other surface treatment, e.g., a MESA coating. Hydrophilic layer 150 can have a thickness, for example, of approximately 100 um. Moreover, in the embodiment of FIGS. 1-5, hydrophilic layer 150 is patterned to provide an air vent for second sample-receiving chamber 164 (as depicted by the alignment of the patterned hydrophilic layer 150 and patterned spacer layer 140 in FIGS. 1 and 2).

Enzymatic reagent layer 130 can include any suitable enzymatic reagents, with the selection of enzymatic reagents being dependent on the analyte to be determined. For example, if glucose is to be determined in a blood sample, enzymatic reagent layer 130 can include a glucose oxidase or glucose dehydrogenase along with other components necessary for functional operation. Enzymatic reagent layer 130 can include, for example, glucose oxidase, tri-sodium citrate, citric acid, polyvinyl alcohol, hydroxyl ethyl cellulose, potassium ferrocyanide, antifoam, cabosil, PVPVA, and water. Further details regarding enzymatic reagent layers, and electrochemical-based analytical test strips in general, are in U.S. Pat. Nos. 6,241,862 and 6,733,655, the contents of which are hereby fully incorporated by reference.

Electrochemical-based analytical test strip 100 can be manufactured, for example, by the sequential aligned formation of patterned conductor layer 120, enzymatic reagent layer 130, patterned spacer layer 140, hydrophilic layer 150 and top layer 160 onto electrically-insulating substrate layer 110. Any suitable techniques known to one skilled in the art can be used to accomplish such sequential aligned formation, including, for example, screen printing, photolithography, photogravure, chemical vapour deposition and tape lamination techniques.

Figure 6:
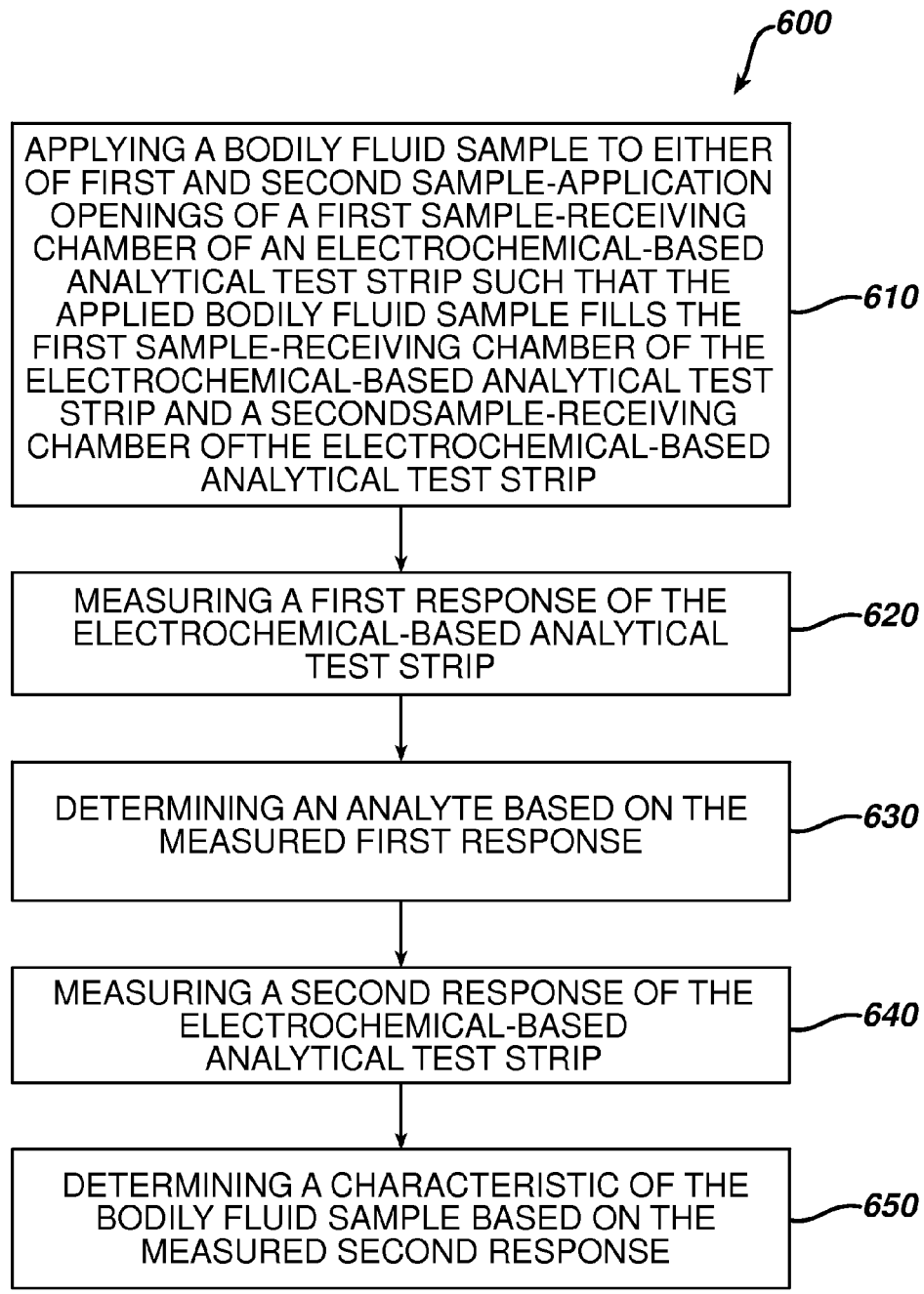
FIG. 6 is a flow diagram depicting stages in a method for determining an analyte in a bodily fluid sample according to an embodiment of the present invention.

FIG. 6 is a flow diagram depicting stages in a method 600 for determining an analyte (such as glucose) in a bodily fluid sample (for example, a whole blood sample) and/or a characteristic of the bodily fluid sample (e.g., hematocrit) according to an embodiment of the present invention. Method 600 includes (see step 610 of FIG. 6) applying a bodily fluid sample to either of a first sample-application opening and a second sample-application opening of a first sample-receiving chamber of an electrochemical-based analytical test strip such that the applied bodily fluid sample fills the first sample-receiving chamber and a second-sample-receiving chamber of the electrochemical-based analytical test strip.

Method 600 also includes measuring a first response of the electrochemical-based analytical test strip (for example an electrochemical response from electrodes in the second sample-receiving chamber) and determining an analyte in the bodily fluid sample is determined based on the measured first response (see steps 620 and 630 of FIG. 6).

In steps 640 and 650 of method 600 also includes, measuring a second response of the electrochemical-based analytical test strip (for example, an electrical response from electrodes in the first sample-receiving chamber) and determining a characteristic of the bodily fluid sample (such as hematocrit or other bodily fluid sample characteristic that can be determined in a reagent-less manner) based on the second measured response. Alternatively, since the first sample-receiving chamber is reagent-less, steps 640 and 650 can be employed to measure a second analyte (such as, for example, uric acid, acetaminophen or dopamine) of the bodily fluid sample in a reagent-less manner. The measuring and determination steps described above can, if desired, by performed using a suitable associated meter and measurement steps 620 and 630 can be performed in any suitable sequence or in an overlapping manner.

Once apprised of the present disclosure, one skilled in the art will recognize that method 600 can be readily modified to incorporate any of the techniques, benefits and characteristics of electrochemical-based analytical test strips according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. An electrochemical-based analytical test strip for the determination of an analyte in a bodily fluid sample, the electrochemical-based analytical test strip comprising:
   a first sample-receiving chamber with:
      a first sample-application opening; and
      a second sample-application opening;
   a first electrode disposed in the first sample-receiving chamber between the first sample-application opening and the second sample-application opening;
   a second electrode disposed in the first sample-receiving chamber between the first sample-application opening and the second sample-application opening;
   a second sample-receiving chamber that intersects the first sample-receiving chamber between the first electrode and the second electrode, thereby defining a chamber intersection, and
   at least a third electrode disposed in the second sample-receiving chamber, including a first working electrode, a second working electrode and a counter/reference electrode.

2. The electrochemical-based analytical test strip of claim 1 wherein the first working electrode, a second working electrode and a counter/reference electrode are configured for the determination of an analyte of a bodily fluid sample in the second sample-receiving chamber.

* * * * *